(12) United States Patent
Bissah et al.

(10) Patent No.: US 8,079,992 B2
(45) Date of Patent: Dec. 20, 2011

(54) STRETCHABLE ABSORBENT ARTICLE

(75) Inventors: Kofi A. Bissah, Somerset, NJ (US); Tarun K. Arora, Edison, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 97 days.

(21) Appl. No.: 11/550,477

(22) Filed: Oct. 18, 2006

(65) Prior Publication Data

US 2007/0299413 A1    Dec. 27, 2007

Related U.S. Application Data

(60) Provisional application No. 60/815,368, filed on Jun. 21, 2006.

(51) Int. Cl.
*A61F 13/15* (2006.01)
*A61F 13/20* (2006.01)

(52) U.S. Cl. .................................... 604/385.01; 604/387

(58) Field of Classification Search .................. 604/358, 604/378, 385.01, 385.03, 387
See application file for complete search history.

(56) References Cited

U.S. PATENT DOCUMENTS

| | | | | |
|---|---|---|---|---|
| 3,397,697 A * | 8/1968 | Rickard | | 604/370 |
| 4,738,676 A * | 4/1988 | Osborn, III | | 604/385.05 |
| 4,940,462 A * | 7/1990 | Salerno | | 604/387 |
| 5,009,653 A * | 4/1991 | Osborn, III | | 604/385.04 |
| 5,484,636 A * | 1/1996 | Berg et al. | | 428/41.8 |
| 5,658,269 A | 8/1997 | Osborn, III | | |
| 5,683,375 A * | 11/1997 | Osborn et al. | | 604/385.16 |
| 5,702,382 A | 12/1997 | Osborn, III | | |
| 5,964,741 A * | 10/1999 | Moder et al. | | 604/358 |
| 6,042,575 A * | 3/2000 | Osborn et al. | | 604/387 |
| 6,572,597 B1 * | 6/2003 | Nash | | 604/385.05 |
| 2004/0068247 A1* | 4/2004 | Connor | | 604/387 |
| 2006/0110564 A1* | 5/2006 | Connor | | 428/41.7 |
| 2006/0173434 A1 | 8/2006 | Zoromski | | |

FOREIGN PATENT DOCUMENTS

| | | |
|---|---|---|
| EP | 0784459 B1 | 2/2004 |
| WO | 97/39712 A1 | 10/1997 |

OTHER PUBLICATIONS

European Search Report dated Jun. 10, 2010 for corresponding EPA No. 07252509.0.

* cited by examiner

*Primary Examiner* — Michelle M Kidwell

(57) ABSTRACT

A multi-layer absorbent article including a first layer and a second layer, the article being constructed such that it is elastic in a longitudinal direction of the article so that a loading force of 400 g extends a sample of the article taken along the longitudinal centerline of the article between about 5% and 20% of the sample's original length, and the recovery of the sample after the loading force is removed at least 90%.

3 Claims, 3 Drawing Sheets

STRETCHABLE ABSORBENT ARTICLE

CROSS-REFERENCE TO RELATED APPLICATIONS

This application claims priority of U.S. Provisional Patent Application No. 60/815,368, filed on Jun. 21, 2006.

FIELD OF THE INVENTION

The present invention relates to absorbent sanitary articles. The present invention is particularly related to pantiliners and will be described herein with reference to a pantiliner, however the present invention has applications to other absorbent sanitary articles such as sanitary napkins, incontinence articles and the like.

BACKGROUND OF THE INVENTION

Disposable absorbent articles, such as pantiliners, sanitary napkins, interlabial devices, adult incontinence devices and diapers are well known in the art. These articles typically have a fluid permeable body facing layer and a fluid impermeable garment facing layer. Additionally, such articles may include an absorbent layer for retaining fluids arranged between the body facing layer and the garment facing layer.

Absorbent articles of the type described above are generally adapted to be placed in the user's undergarment and may optionally include an adhesive arranged on the garment facing surface of the article for attachment of the article to the garment. A problem with absorbent articles of the type disclosed in the prior art is that they do not behave in the same manner as the user's undergarment which can result in a number of comfort and functional shortcomings. In particular, due to the fact that the absorbent article does not behave in the same manner as the user's undergarment, the user may be aware of the article during use which can be distracting and uncomfortable. For example, if the absorbent article is significantly stiffer than the user's undergarment, the user may feel the article as a distinct structure from the undergarment which may cause discomfort. Likewise, if the article is not sufficiently stretchable the absorbent article may not deform in the same manner as the underwear, again making the user aware the absorbent article in a distracting manner.

As mentioned above, many absorbent articles include a garment facing adhesive for securing the absorbent article to garment. If the absorbent article is constructed such that it is significantly more stretchable than the garment to which it is attached, the absorbent article will deform during use in a manner that is significantly different than the garment to which it is attached. This behavior results in a relatively high shear force being exerted on the adhesive that attaches the absorbent article to the undergarment, thereby causing the absorbent article to detach from the undergarment during use.

In view of the foregoing, it is an object of the present invention to provide an improved absorbent article that behaves like underwear during use thereby improving comfort and insuring secure attachment of the absorbent article to the underwear during use.

SUMMARY OF THE INVENTION

In view of the above objectives, the present invention provides, according to a first aspect of the invention, a multi-layer absorbent article including at least a first layer, at least a second layer, wherein the article is elastic in a longitudinal direction of the article such that a loading force of 400 g extends a sample of the article taken along the longitudinal centerline of the article between about 5% and 20% of the sample's original length, and the recovery of the sample after the loading force is removed is at least 90%.

The present invention provides, according to a second embodiment of the invention, a multi-layer absorbent article including at least a first layer, at least a second layer, wherein the article is elastic in a longitudinal direction of the article such that a loading force of 400 g extends a sample of the article taken along the longitudinal centerline of the article between about 7% and 14% of the sample's original length, and the recovery of the sample after the loading force is removed is 100%, wherein the article has a MCB of less than about 25 g, wherein the article has a thickness of less than about 1 mm, and wherein the article has an absorbent capacity of less than about 2 g.

DETAILED DESCRIPTION OF THE INVENTION

The present invention is particularly related to pantiliners and will be described herein with reference to a pantiliner, however the present invention has applications to other absorbent sanitary articles such as sanitary napkins, incontinence articles and the like.

The term "elastic" as used herein means that the article or the layer being referenced tends to deform when subjected to an external load and recovers, at least partially, from said deformation when the load is removed.

The term "stretchable" as used herein means that the article or the layer being referenced tends to deform when subjected to an external load but does not recover from said deformation when the load is removed.

In order to provide the pantiliner according to the present invention with the required elastic properties, at least one of the layers of the article must be elastic, and all of the layers must be stretchable. However, it is not required that all of the layers be elastic. It has been found that the article as a whole has the necessary elastic properties even if some of the layers are stretchable but not elastic, provided that the article includes at least one elastic layer.

Figure 1:
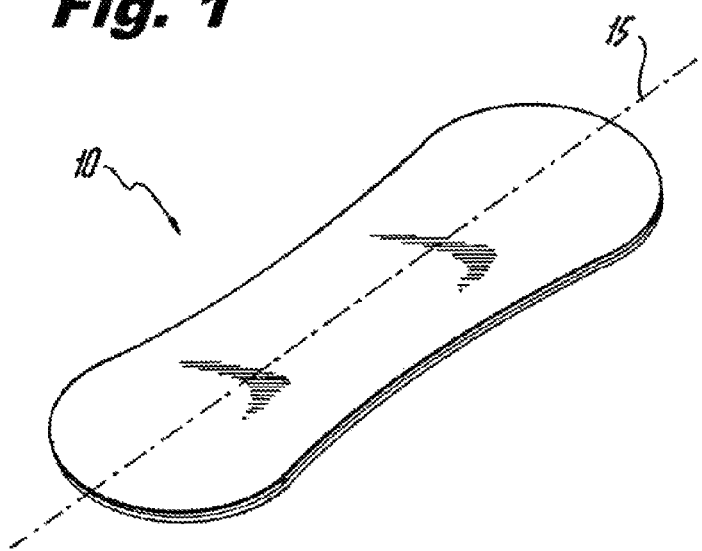
FIG. 1 is a perspective view of a pantiliner according to the present invention.
Figure 2:
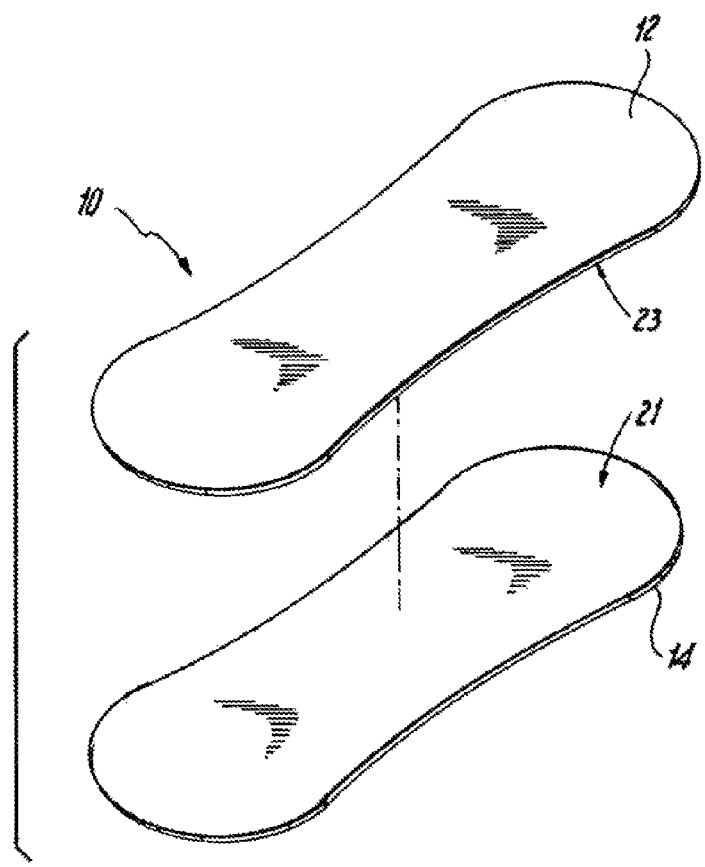
FIG. 2 is an exploded perspective view of the pantiliner shown in FIG. 1.

Reference is made to FIGS. 1 and 2, which depict a pantiliner 10 according to the present invention. In the embodiment of the invention shown in FIGS. 1 and 2, the pantiliner 10 includes a liquid permeable body facing layer 12 (also referred to herein as the "cover layer") and a liquid impermeable garment facing layer 14 (also referred to herein as the "barrier layer"). In one embodiment of the present invention the body facing layer 12 is constructed from a material that is stretchable but not elastic and the garment facing layer 14 is constructed from a layer that is elastic. Alternatively, it is possible that both of the layers 12 and 14 could be constructed from elastic materials. A longitudinally extending centerline of the pantiliner is identified by the reference numeral 15.

Figure 3:
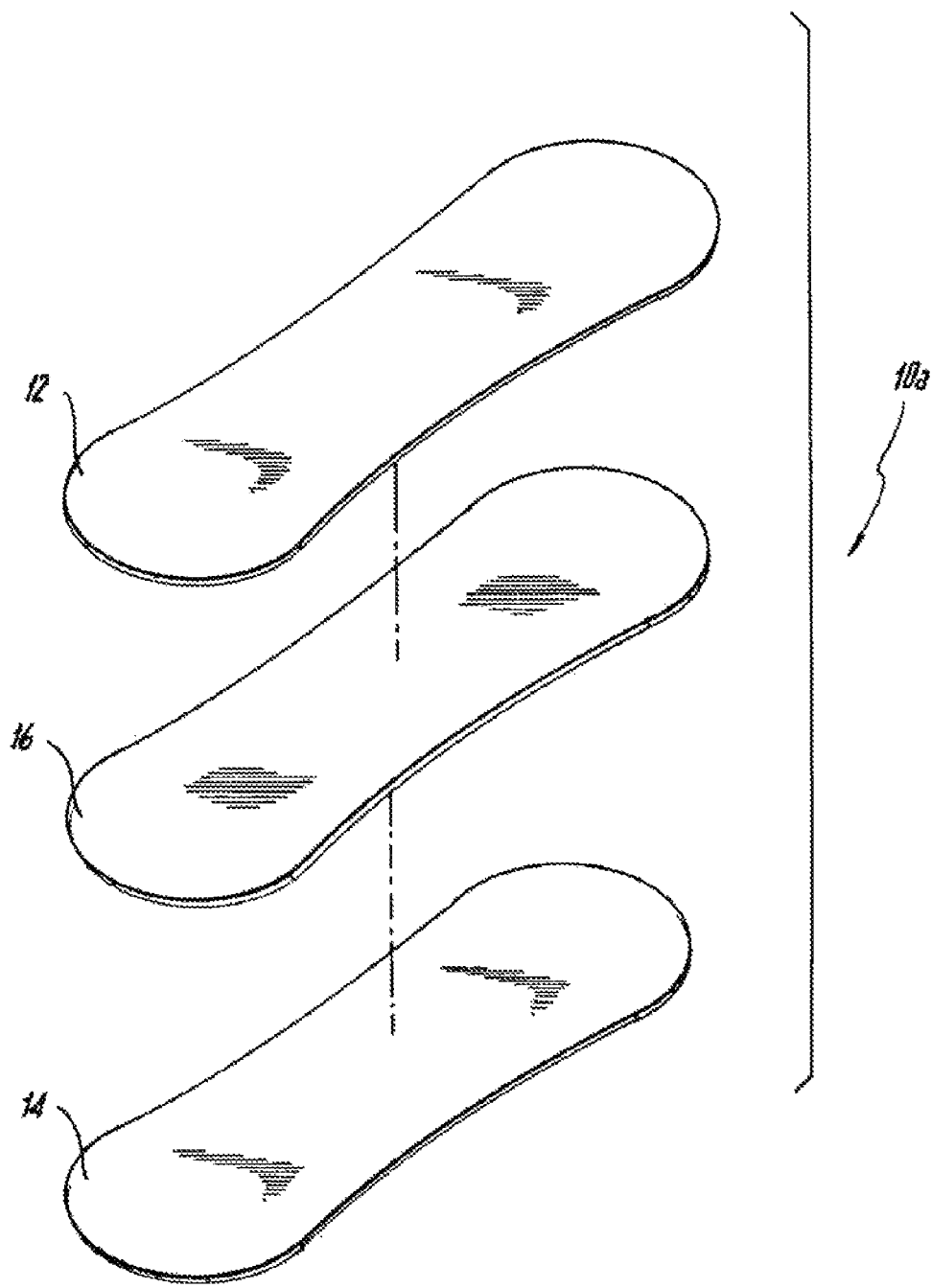
FIG. 3 is an exploded perspective view an alternate embodiment of the pantiliner shown in FIG. 1.

Another embodiment of the pantiliner 10a according to the present invention is shown in FIG. 3. The pantiliner 10a includes a liquid permeable body facing layer 12, a liquid impermeable garment facing layer 14 and an absorbent system 16 arranged between the layers 12 and 14.

Each of the layers 12, 14 and 16 are discussed in greater detail below. In addition, preferred functional properties of the pantiliner according to the present invention are discussed in detail below together with the test methods for measuring said functional properties.

Body Facing Layer

The body facing layer 12 preferably comprises a liquid permeable material that is stretchable when subjected to an external load. Alternatively the body facing layer 12 may comprise a liquid permeable material that is elastic. The body facing layer 12 should be selected to provide the article with the preferred flexibility, absorbency, thickness, and elongation/recovery properties described in detail below.

The body facing layer 12 may be a relatively low density, bulky, high-loft non-woven web material. The body facing layer 12 may be composed of only one type of fiber, such as polyester or polypropylene or it may include a mixture of more than one fiber. The body facing layer 12 may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the body facing layer 12 has a basis weight in the range of about 50 gsm (g/m$^2$) to about 100 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the body facing layer 12 may be mounted to the absorbent layer 16 and/or to the barrier layer 14.

The body facing layer 12 preferably has a relatively high degree of wettability, although the individual fibers comprising the cover may not be particularly hydrophilic. The body facing layer 12 should also contain a great number of relatively large pores. This is because the body facing layer 12 is intended to take-up body fluid rapidly and transport it away from the body and the point of deposition.

Advantageously, the fibers which make up the body facing layer 12 should not lose their physical properties when they are wetted, in other words they should not collapse or lose their resiliency when subjected to water or body fluid. The body facing layer 12 may be treated to allow fluid to pass through it readily. The body facing layer 12 also functions to transfer the fluid quickly to the other layers of the absorbent system 16, if such absorbent system 16 is employed. Thus, the body facing layer 12 is advantageously wettable, hydrophilic and porous. When composed of synthetic hydrophobic fibers such as polyester or bi-component fibers, the body facing layer 12 may be treated with a surfactant to impart the desired degree of wettability.

In one preferred embodiment of the present invention the body facing layer 12 is made from a spunlace nonwoven material having from about 0 to about 100% polyester and from about 0 to about 100% rayon. The spunlace material may also be made from about 10% to about 65% rayon and from about 35% to about 90% polyester. In lieu of, and/or in combination with the polyester, polyethylene, polypropylene or cellulosic fiber may be used with the rayon. Optionally, the material used for the body facing layer 12 may include binders such as thermoplastic binders and latex binders, provided that such binders are not included to such an extent as to prevent the body facing layer from being stretchable. One suitable commercially available cover material is a spunlace nonwoven material available from Polymer Group Inc., Charleston, S.C. under product code 4012

Alternatively, the body facing layer 12 can also be made of polymer film having large pores. Because of such high porosity, the film accomplishes the function of quickly transferring body fluid to the inner layers of the absorbent system 16.

The body facing layer 12 may be embossed to the absorbent system 16 in order to aid in promoting hydrophilicity by fusing the cover to the next layer. Such fusion may be effected locally, at a plurality of sites or over the entire contact surface of the body facing layer 12 and the absorbent system 16. Alternatively, the body facing layer 12 may be attached to the absorbent 16 by other means such as by adhesion.

Absorbent System

The absorbent system 16 may comprise a single layer of material or may comprise multiple layers. The absorbent system 16 may comprise a blend or mixture of cellulosic fibers and superabsorbent disposed therein.

Cellulosic fibers that can be used in the absorbent system 16 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material.

The absorbent system 16 can contain any superabsorbent polymer (SAP) which are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

In one embodiment of the invention, the absorbent system 16 consists entirely of superabsorbent polymer that is arranged between the body facing layer 12 and the garment facing layer 14. For example, the absorbent system may consist of superabsorbent polymer adhered to an internal surface 21 of the garment facing layer 14 and/or the internal surface 23 body facing layer 12 using a suitable adhesive.

Garment Facing Layer

Underlying the body facing layer 12, and/or the absorbent system 16 if such system is employed, is a garment facing layer 14 that is liquid impermeable. In a preferred embodiment of the invention the garment facing layer 14 is elastic. The garment facing layer 14 is preferably made of polymeric film, although it may be made of liquid impervious, air-permeable material such as repellent-treated non-woven or micropore films or foams. Preferably the garment facing layer 14 has a basis weight in the range of about 20 gsm to about 40 gsm. One suitable commercially available garment facing layer 14 is a polymer film material commercially available from Tredegar Film Products, Lake Zurich, Ill. under product code X31468.

The garment facing layer 14 may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet.

The body facing layer 12 and the garment facing layer 14 are joined along their marginal portions so as to form a flange seal. The joint may be made by means of adhesives, heat-bonding, ultrasonic bonding, radio frequency sealing, mechanical crimping, and the like and combinations thereof.

In a preferred embodiment of the invention positioning adhesive is applied to a garment facing side of the garment facing layer 14 for securing the liner 10 to the garment during use. The positioning adhesive may be covered with a removable release paper so that the positioning adhesive is covered by the removable release paper prior to use.

The positioning adhesive may comprise a suitable pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof; hot melt adhesives based on suitable block copoylmers—suitable block copolymers for use in the invention include linear or radial co-polymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Example 1

An absorbent article according to the present invention, a pantiliner, was constructed as follows:
(1) A liquid permeable body facing layer constructed from a spunlace nonwoven material having a basis weight of 75 gsm commercially available from Polymer Group Inc., Charleston, S.C. under product code 4012.
(2) An elastic liquid impermeable garment facing polymer film layer, having a basis weight of 23 gsm, commercially available from Tredegar Film Products, Lake Zurich, Ill., under product code X31468.

Figure 4:
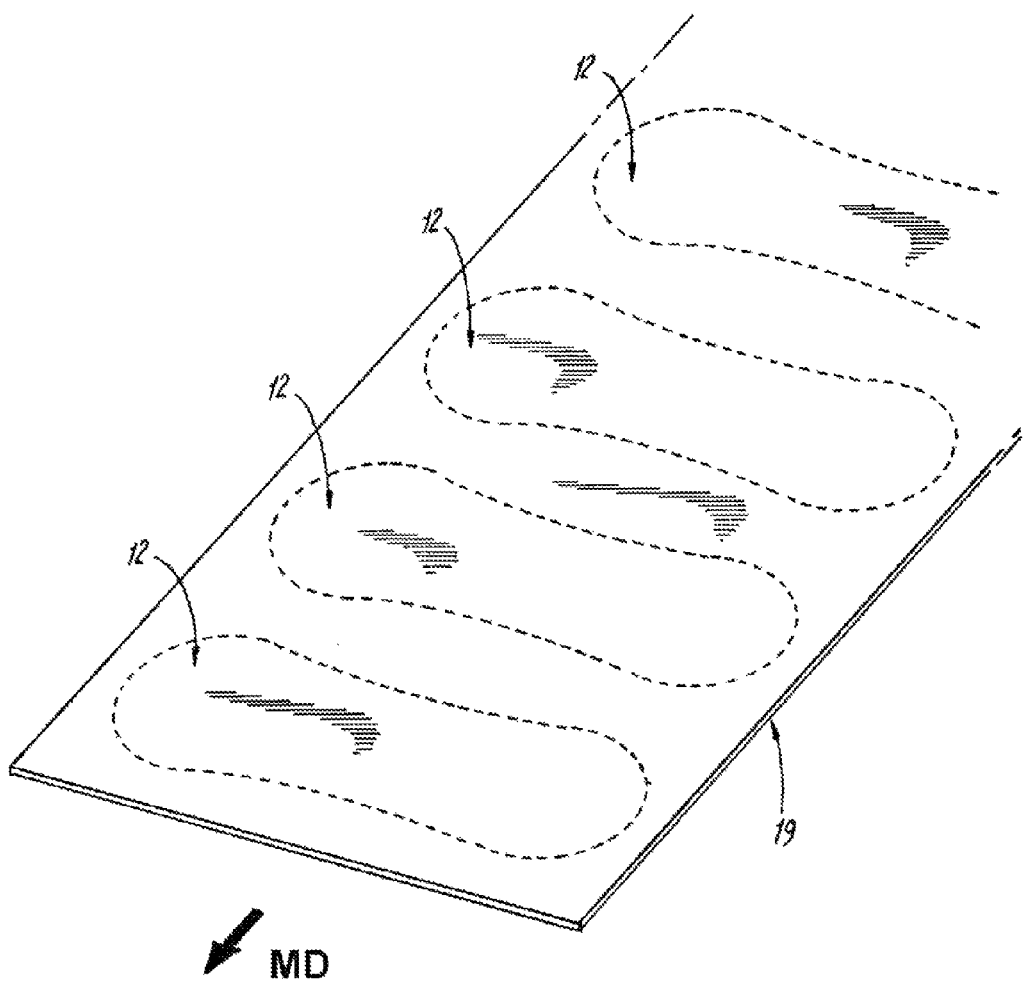
FIG. 4 is a schematic view showing the orientation in which the body facing layer is cut from a rolled nonwoven web material.

The body facing layer was arranged on top of the garment facing layer such that the machine direction of the body facing material was arranged in the transverse direction of the article. Stated another way, during manufacture the body facing layer 12 was cut from the rolled web material 19 as shown in FIG. 4. The machine direction of the rolled web material 19, is identified by the designation MD in FIG. 4. The two layers were adhered together by slot coating a construction adhesive (Fuller HL1023, commercially available from H. B. Fuller, St. Paul, Minn.) in the amount of 6.3 mg/sq. in. in a 68 mm wide band on the internal surface of the garment facing layer. The body facing layer was then arranged on top of the adhesive to adhere the two layers together. A positioning adhesive layer (Fuller NW 1042ZP, commercially available from H. B. Fuller, St. Paul, Minn.) was applied to the garment facing surface of the garment facing layer in the amount of 9.98 mg/sq in. in a 54 mm wide strip.

Procedure for Measuring Modified Circular Bend Stiffness (MCB)

Absorbent articles according to the present invention are preferably highly drapeable. As used herein, the terms "drapeable" and "drapability" are used interchangeably and mean having a flexural resistance of about 35 g or less as tested by the Modified Circular Bend Test, ASTM 4032-82 as described in further detail below. The terms flexural resistance and MCB are used interchangeable herein. Articles according to the present invention preferably have a flexural resistance (MCB), of less than about 35 g, more preferably less than about 25 g or less, and most preferably about 20 g or less. It has been found that, for example, cotton underwear (e.g., Hanes Cotton underwear) has a flexural resistance of less than 35 g. The procedure for determining MCB is provided in detail below.

Modified Circular Bend Stiffness (MCB) is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:
1. A smooth-polished steel plate platform, which is 102.0 mm by 102.0 mm by 6.35 mm having an 18.75 mm diameter orifice. The lap edge of the orifice should be at a 45 degree angle to a depth of 4.75 mm;
2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;

3. A force-measurement gauge and more specifically an Instron inverted compression load cell. The load cell has a load range of from about 0.0 to about 2000.0 g;

4. An actuator and more specifically the Instron Model No. 1122 having an inverted compression load cell. The Instron 1122 is made by the Instron Engineering Corporation, Canton, Mass.

In order to perform the procedure for this test, as explained below, three representative product samples for each article are necessary. The location of the sanitary napkin, or other absorbent article, to be tested is selected by the operator, provided that the test specimen is taken from an absorbent portion of the article. A 37.5 mm by 37.5 mm test specimen is cut from each of the three product samples at corresponding locations. Prior to cutting the samples any release paper or packaging material is removed and any exposed adhesive, such as garment positioning adhesive, is covered with a non-tacky powder such as talc or the like. The talc should not affect the MCB measurements.

The test specimens should not be folded or bent by the test person, and the handling of specimens must be kept to a minimum and to the edges to avoid affecting flexural-resistance properties.

The procedure for the CIRCULAR BEND PROCEDURE is as follows. The specimens are conditioned by leaving them in a room that is 21° C., +/−1° C. and 50%, +/−2.0%, relative humidity for a period of two hours.

A test specimen is centered on the orifice platform below the plunger such that the body facing layer of the specimen is facing the plunger and the barrier layer of the specimen is facing the platform. The plunger speed is set at 50.0 cm per minute per full stroke length. The indicator zero is checked and adjusted, if necessary. The plunger is actuated. Touching the test specimen during the testing should be avoided. The maximum force reading to the nearest gram is recorded. The above steps are repeated until all of three specimens have been tested. An average is then taken from the three test values recorded to provide an average MCB stiffness in grams.

Procedure for Measuring Average Absorbent Capacity (AC)

Articles according to the present invention preferably have an absorbent capacity less than about 5 g, more preferably less than about 3 g and most preferably about 1 g. The procedure for determining absorbent capacity is provided below.

At least three new product samples are required to the conduct the average absorbent capacity test described below. The specimens are conditioned by leaving them in a room that is 21° C., +/−1° C. and 50%, +/−2.0%, relative humidity for a period of two hours.

The average absorbent capacity test is conducted on a 37.5 mm×37.5 mm square test specimen cut from the product sample. The cut square 37.5 mm×37.5 mm test specimen is taken from the corresponding product location as those samples taken from the products used in the MCB test described above.

Prior to doing the test, at least six 60 mm×60 mm square envelopes are constructed from a lightweight nonwoven such as 0.7 ounce per sq yard through air bonded web of bicomponent fibers. A suitable example of the nonwoven material is commercially available from Polymer Group, Inc., Charleston, S.C., under product code 4128. The envelope can be formed by folding a 120 mm×60 mm square section and heat sealing the sides with the sample enclosed. Other envelope constructions can be use as long as they permit unhindered absorption of the test fluid to the sample during the submergence portion of the test and unhindered dripping during the dripping portion.

An envelope, without the test specimen, is submerged in a saline solution (0.9%) for 15 minutes, and then hung so that saline can freely drip for 12 minutes. The wet weight of the envelope is then measured to the nearest one hundredth of a gram. This procedure is conducted for three envelope samples and the average wet weight of the envelope is determined.

The weight of each of the three dry 37.5 mm×37.5 mm test specimens is measured before beginning the test. A 37.5 mm×37.5 mm test specimen is inserted in an dry envelope and the envelope is submerged in a saline solution (0.9%) for 15 minutes and then hung so that saline can freely drip for 12 minutes. The wet weight of the combined envelope and test specimen are then measured to the nearest one hundredth of a gram. The dry weight of the test specimen and the average wet weight of the envelope alone are then subtracted to determine the absorbent capacity of the test specimen.

This is repeated for three 37.5 mm×37.5 mm test specimens and the absorbent capacity average is taken to provide the average absorbent capacity (AC).

Procedure for Measuring the Thickness of an Absorbent Article

Articles according to the present invention preferably have a thickness of less than about 3 mm, more preferably less than about 2 mm, and most preferably less than about 1 mm. The procedure for determining the thickness of an absorbent article is provided below.

The thickness measurement procedure described below should be conducted on three product samples prior to conducting the MCB test described above after the product samples have been removed from any packaging, any release paper has been removed, and after the product has been powdered with talc or the like. The thickness measurement of the product should be conducted at the same location from which the test specimen for the MCB test will be taken.

The apparatus required to measure the thickness of an absorbent article is a footed dial (thickness) gauge with stand, available from Ames, with a 2" (5.08 cm) diameter foot at a pressure of 0.07 psig and a readout accurate to 0.001" (0.00254 cm). A digital type apparatus is preferred. If the sanitary napkin sample is individually folded and wrapped, the sample is unwrapped and carefully flattened by hand. The release paper is removed from the product sample and it is repositioned back gently across the positioning adhesive lines so as not to compress the sample, ensuring that the release paper lies flat across the sample. Flaps (if any) are not considered when taking the thickness reading.

The foot of the gauge is raised and the product sample is placed on the anvil such that the foot of the gauge is approximately centered on the on the location of interest on the product sample. When lowering the foot, care must be taken to prevent the foot from dropping onto the sample or from undue force being applied. A load of 0.07 p.s.i.g. is applied to the sample and the read out is allowed to stabilize for approximately 5 seconds. The thickness reading is then taken. This procedure is repeated for at least three product samples and the average thickness is then calculated.

Procedure for Measuring Elongation and Recovery

Eight identically constructed product samples are required to conduct the Procedure for Measuring Elongation and Recovery set forth below.

Elongation is determined by a test that is modeled after the ASTM D 5035-90 ELONGATION OF TEXTILE FABRICS, the procedure being considerably modified as described herein (hereinafter referred to as the "ELONGATION TEST"). The ELONGATION TEST compares applied force and percent elongation of the test sample.

The apparatus necessary for the ELONGATION TEST is a tensile testing machine with clamps capable of grasping the test sample. The tensile testing machine is interfaced with a computer to provide a readout of the measured force and elongation. The tensile testing apparatus used to obtain the values set forth herein is the Instron Model No. 1122 having an inverted tension load cell (Catalogue #2511-603, Serial #260). The Instron 1122 is made by the Instron Engineering Corporation, Canton, Mass.

The absorbent articles to be tested are conditioned by leaving them in a room that is 21° C., +/−1° C. and 50%, +/−2.0%, relative humidity for a period of two hours.

The ELONGATION TEST is performed as follows:

(1) A 1.0" wide×5.0" long test sample is cut along the longitudinal centerline of the absorbent article to be tested. The sample should be cut from the product such that the center of the sample corresponds in location to the location of the absorbent article intended to be placed over the vaginal opening during use of the article.

(2) Each end of the test sample is arranged in one of test jaws of the Instron such that the end of the test strip is centered within the test jaw and a one inch (1") portion of the test strip is arranged in each jaw. In this manner, a three inch (3") portion of each strip is arranged between the jaws of the Instron.

(3) The constant air pressure setting on the Instron apparatus is selected to insure that the test sample does not slip during the test.

(4) The cross head speed of the Instron apparatus is set to a speed of 5"/minute.

(5) A first test strip taken from a first one of the product samples is subjected to a load of 100 g and the percent elongation of the strip under the 100 g load is recorded. A second test strip taken from a second one of the product samples is subjected to a load of 100 g and the percent elongation of the second strip under the 100 g load is recorded. The percent elongation for the first and second strip are then averaged to provide an average elongation at 100 g. The percent elongation is provided directly by a print out from the test apparatus or it may be manually determined by measuring the length of the sample under load and comparing it to the original length of the sample. For example percent elongation may be represented by the following formula:

$$\% \text{ Elongation} = ((Ld-Lo)/Lo)*100; \text{ where}$$

Ld=Length of the sample under load;
Lo=Original length of the sample, for purposes of this test method Lo=5.0".

The above procedure is repeated for two new test trips at 200 g, two test strips at 300 g and two test strips at 400 g. Thus a total a eight strips are tested and an average elongation is calculated at 100 g, 200 g, 300 g and 400 g. The calculated average percent elongation for samples taken from products constructed in accordance with Example 1 are set forth in the chart below.

After each sample is elongated and removed from the Instron the sample is permitted to recover from deformation for a period of thirty (30) seconds. The length of the sample after deformation, i.e. the final length (Lf) of the sample, is then manually determined by measuring the length of the sample. The percent recovery of the sample is calculated as follows:

$$\% \text{ Recovery} = [1-((Lf-Lo)/Lo)]*100; \text{ where}$$

Lf=Final measured length of the sample after removed from load;
Lo=Original length of the sample, for purposes of this test method Lo=5.0"

The percent recovery for each sample is determined and an average percent recovery for the two samples deformed under the load of 100 g is then calculated. The average percent recovery for the two samples under the load 200 g is then calculated. In this same manner, the average percent recovery is also calculated for the 300 g load and 400 g load samples.

Tables 1 and 2 set forth below provides the values measured in accordance with the ELONGATION TEST for a product constructed as described in "Example 1" above.

TABLE 1

Example 1, % Elongation

| Applied Force (g) | % Elongation |
|---|---|
| 100 | 1.82 |
| 200 | 3.1 |
| 300 | 4.83 |
| 400 | 7.77 |

TABLE 2

Example 1, % Recovery

| Applied Force (g) | Original Length - Lo (in.) | Final Length - Lf (in.) | % Recovery |
|---|---|---|---|
| 100 g | 5.0 in. | 5.0 in. | 100% |
| 200 g | 5.0 in. | 5.0 in. | 100% |
| 300 g | 5.0 in. | 5.0 in. | 100% |
| 400 g | 5.0 in. | 5.0 in. | 100% |

The absorbent article as described in Example 1 was also tested for MCB, absorbent capacity and thickness according to the test methods described above and the article had an MCB of 20 g, an absorbent capacity of 0.95 g and a thickness of 0.85 mm.

In view of the above the present invention provides an absorbent article that behaves like the garment to which it is attached during use thereby providing enhanced comfort and insuring that the article remains securely attached to the garment during use.

What is claimed is:

1. A multi-layer absorbent article comprising:
   at least a first stretchable layer;
   at least a second layer;
   wherein the article is elastic in a longitudinal direction of the article such that a loading force of 400 g extends a sample of said article taken along the longitudinal centerline of the article between about 7% and 14% of the sample's original length, and the recovery of said sample after said loading force is removed is 100%;
   wherein said article has a MCB of less than about 25 g;
   wherein said article has a thickness of less than about 1 mm; and
   wherein said article has an absorbent capacity of less than about 2 g.

2. The absorbent article according to claim 1, wherein said absorbent article is one of a panty liner, sanitary napkin and incontinence article.

3. A multi-layer absorbent article consisting of:
   a first stretchable layer;
   a second layer;

wherein the article is elastic in a longitudinal direction of the article such that a loading force of 400 g extends a sample of said article taken along the longitudinal centerline of the article between about 7% and 14% of the sample's original length, and the recovery of said sample after said loading force is removed is 100%;

wherein said article has a MCB of less than about 25 g;

wherein said article has a thickness of less than about 1 mm; and wherein said article has an absorbent capacity of less than about 2 g.

* * * * *